US006696422B2

(12) United States Patent
Hirschman

(10) Patent No.: US 6,696,422 B2
(45) Date of Patent: Feb. 24, 2004

(54) COMBINATION THERAPY FOR HIV INFECTIONS

(75) Inventor: Shalom Z. Hirschman, Riverdale, NY (US)

(73) Assignee: Advanced Viral Research Corp., Hallandale, FL (US)

( * ) Notice: Subject to any disclaimer, the term of this patent is extended or adjusted under 35 U.S.C. 154(b) by 18 days.

(21) Appl. No.: 09/316,374

(22) Filed: May 21, 1999

(65) Prior Publication Data

US 2001/0005712 A1 Jun. 28, 2001

Related U.S. Application Data

(63) Continuation-in-part of application No. 08/922,888, filed on Sep. 3, 1997, now abandoned, which is a continuation-in-part of application No. 08/839,649, filed on Apr. 15, 1997, now abandoned.

(51) Int. Cl.$^7$ .............................................. A61K 48/00
(52) U.S. Cl. .............................. 514/44; 514/2; 514/21; 424/529
(58) Field of Search .............................. 424/520, 278.1; 514/2, 21, 44; 530/300; 435/87

(56) References Cited

U.S. PATENT DOCUMENTS 5,597,824 A    1/1997    Norbeck et al.

OTHER PUBLICATIONS

Ho et al., Seminars in Oncology, vol. 24, 2, pp. 187–220, 1997.*
Gilden et al. (GMHC Treat Issues, vol. 10, 3, pp. 1–5), 1996.*
Stull et al. Pharmaceutical Research, vol. 12, 4, p. 476, col. 2, last paragraph, 1995.*
Reynolds, Margaret R., Generalized Vaccinia, Symposium, pp. 5–6, 1960.
Kuckku, Morris E., Herpetic Diseases, Symposium, pp. 7–13, 1960.
Schaeffer, Oden A., Influenza, Symposium, pp. 15–21, 1960.
Seydel, Frank, Epidemic, Asian Influenza, Symposium, pp. 23–24, 1960.
Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Florida, pp. 25–32.
Medoff, Lawrence R., Infectious Mononucleosis, Symposium, pp. 33–37, 1960.
Anderson, Robert H., Encephalitis, Symposium, pp. 39–52, 1960.
Plucinski, Stanisloff J., Suspected Viral Varieties, Symposium, pp. 53–59, 1960.
Kosaka, K. and Shimada, Y., Infectious Hepatitis, Symposium, pp. 61–74, 1960.

Anderson, Robert H. and Thompson, Ralph M., Treatment of Viral Syndrome with a Lipoprotein–Nucleic Acid Compound (Reticulose), A Report of Five Cases, Virginia Medical Monthly, 84: 347–353, 1957.
Reynolds, Margaret R., Generalized Vaccinia Successfully Treated With Lipoprotein–Nucleic Acid Complex (Reticulose), Archives of Pediatrics, 77:421–422, 1960.
Wegryn, Stanley P., Marks, Robert A. and Baugh, John R., Herpes Gestationis, A Report of 2 Cases, American Journal of Obstetrics and Gynecology, 79:812–814, 1960.
Catterall, R.A., Lumpur, Kuala, A New Treatment of Herpes Zoster, Vaccinia And Chicken Pox, J. Roy. Coll. Gen. Practit., 1970, 19, 182.
Chinnici, Angelo A., Reticulose in Treatment Aids patients, Personal Communication to William Bregman, Jul. 6, 1992.
Cott, Rafael A., Summary of 11 Cases of Viral Infections Treated with Reticulose, Private Communication with Advance Viral Research Corp., 1989.
Cohen, Matthew, The Efficacy of a Peptide–Nucleic Acid Solution (Reticulose) for the Treatment of Hepatitis A and Hepatitis B—a Preliminary Controlled Human Clinical Trial, J. Roy. Soc. Health, Dec., 1992, 266–270.
Mundschenk, David D., In Vitro Antiviral Activity of Reticulose vs Influenaz A, Personal Communication with William Bregman, May 1, 1990.
Resnick, Lionel, Anti–HIV in Vitro Activity of Two Samples of Peptide–nucleic Acid Solution, Personal Communication with Dr. Bernard Friedland, Dec. 22, 1989.
Friedland, Bernard, In Vitro Antiviral Activity of a Peptide–Nucleic Acid Solution Against the Human Immunodeficiency Virus and Influenza A Virus, J. Roy. Soc. Health, Oct. 1991, 170–171.
Brazier, Anne D., Method for in Vitro Antiviral Evaluation Human Immunodeficiency Virus (HIV), Personal Communication with Dr. Bernard Friedland, Oct. 4, 1989.
Behbehani, Abbas M., Haberman Sol and Race, George J, The Effect of Reticulose on Viral Infections of Experimental Animals, Southern Medical Journal, Feb., 1962, 185–188.
Treatment of Viral Diseases with A Lipo–protein Nucleic Acid Complex (Reticulose)—A Clinical Study, Scientific Exhibit: Virginia State Medical Society Meeting, Washington D.C., Nov., 1957.
Kempe, Henry C., Fulginiti, Vincent A., and Vincent, Leone St., Failure to Demonstrate Antiviral Activity of Reticulose, Diseases of Children, vol. 103, No. 5, 655–657, 1962.

(List continued on next page.)

Primary Examiner—Dave T. Nguyen
(74) Attorney, Agent, or Firm—Cohen, Pontani, Lieberman & Pavane

(57) ABSTRACT

The present invention discloses a method of treating patients having AIDS or HIV infections by parenterally administering Product R, a peptide-nucleic acid preparation, in a combination with one or more antiviral agents useful for treating AIDS or HIV infections including HIV protease inhibitors and nucleoside analogs.

6 Claims, No Drawings

OTHER PUBLICATIONS

Sanders, Murray, Controlled Animal Studies with Reticulose Illustrating the Interference of Lipoprotein–Nucleic Acid Complex in the Experimental Animal Infected with Human Pathogenic Viral Entities, Southern Medical Association Scientific Exhibit, Dallas, Texas, Nov., 1961.

XP–001042169 "Reticulose Anti–HIV Trial Results", vol. 9, No. 12 Dec. 1996.

XP–002914304 Treatment of Viral Syndromes with a Lipo–Protein–Nucleic Acid Compound (Reticulose), vol. 84, Jul. 1957.

XP–001042170 "Reticulose Enters Trials for Genital Warts; Shows Anti–HIV Activity", vol. 9, No. 6, Jun. 1996.

XP–002912075 "Peptide Nucleic Acids Stimulate Gamma Interferon and Inhibit the Replication of the Human Immunodeficiency Virus", vol. 44, No. 6, Aug. 1996.

Danner, S.A. et al., "A Short–Term Study of the Safety, Pharmacokinetics, and Efficacy of Ritonavir, and Inhibitor of HIV–1 Protease", vol. 333, No. 23 Dec. 1995.

Geleziunas, R. et al., "Effect of 3'–Azido–3'–Deoxythymidine on Human Immunodeficiency Virus Type 1 Replication in Human Fetal Brain Macrophages", vol. 37, No. 6, Jun. 1993.

Friedland, Bernard, "In Vitro Antiviral Activity of a Peptide–Nucleic Acid Solution Against the Human Immunodeficiency Virus and Influenza A Virus", Joy Roy. Soc. Health, Oct. 1991, pp. 170–171.

* cited by examiner

COMBINATION THERAPY FOR HIV INFECTIONS

CROSS-REFERENCE TO RELATED APPLICATIONS

This application is a continuation-in-part of the application Ser. No. 08/922,888, filed on Sep. 3, 1997, which is a continuation-in-part of the application Ser. No. 08/839,649 filed by Shalom Z. Hirschman on Apr. 15, 1997, entitled "A Combination Therapy For HIV Infections", both now abandoned. Applications Ser. No. 08/922,888 and Ser. No. 08/839,649 are herein incorporated by references in their entireties.

BACKGROUND OF THE INVENTION

I. Field of the Invention

The present invention relates to a method for using Product R as hereinafter defined in combination with other anti-human immunodeficiency virus (HIV) to treat patients having HIV infections.

II. Description of the Related Art

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTL-III, or ARV. The virus specifically attacks T-4 helper lymphocytes, a subgroup of T-lymphocytes that plays a major role in defending the body against infectious diseases. Depletion of this subset of lymphocytes is manifested by an increased incidence of opportunistic infections like pneumocystis carinii and certain cancers. More specifically, the virus enters the T-lymphocyte and incorporates viral encoded DNA into the DNA of the host T-lymphocyte. As long as the infected T-lymphocyte remains inactivated, the virus will quietly remain in the DNA of the host cell. This will not kill the cell but may impair its function. When the infected T-lymphocytes are activated by stimuli such as a specific antigen, the viral DNA in the host DNA is expressed and produces new viral particles. The host T-lymphocyte is then killed and lysed, releasing new viral particles that can invade and kill other T-lymphocytes. The loss of T-4 lymphocytes is profound and occurs even faster than can be accounted for by direct viral killing of the cells. This has led some investigators to postulate that the infection somehow shuts off the production of T-4 lymphocytes. In any case, the normal thymus is no longer functioning and the killed T-lymphocytes cannot be replaced leaving the patient vulnerable to subsequent infections. Especially striking are recent studies of the thymuses of deceased AIDS patients ranging in age from 10 months to 42 years. AIDS victims have profound thymic involution; much more extensive than in age-matched patients who died of other causes.

The cure of a person with AIDS will probably require one agent to eliminate the virus and other agents to cause the body to replace T cells that have been killed by the virus. The first step is to eliminate the AIDS virus from the patient. This will have to be supported by other therapies to induce restoration of immune function. Studies to date with macrophage activating agents, interferon inducers and lymphokines have been disappointing, possibly because their targets, T-lymphocytes, do not exist in sufficient numbers. Interleukin 2 restores the function of one subset of non T-cells (natural killer cells) but has no effect on a host of other serious defects. More drastic measures can be performed.

One potential method of restoring the immune system is by transplanting bone marrow from healthy donors. However, this is a dangerous procedure. It may produce lethal graft versus host disease unless the patient's donor is an identical twin.

A common feature of retrovirus replication is the extensive post-translational processing of precursor polypeptides by a vitally encoded protease to generate mature vital proteins required for virus assembly and function. Inhibition of this processing prevents the production of normally infectious virus. It has been demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV. However, administration of a HIV protease inhibitor sometimes cause side effects including nausea, nephrolithiasis, increased bilirubin, or gastro-intestinal upset.

Zidovudine (AZT) is a synthetic pyrimidine analog that differs from thymidine in having an azido substituent instead of a hydroxyl group at the 3' position of the deoxyribose ring. It was initially developed as an anticancer agent and subsequently found to inhibit the reverse transcriptase (RT) of Friend leukemia virus. Soon after the identification of a human retrovirus as the etiologic agent of AIDS, zidovudine was shown to have anti-HIV activity in vitro. Zidovudine selectivity is due to the preferential interaction of AZT-TP with the RT. Phosphorylation of zidovudine to its active form, AZT-TP, is accomplished by cellular enzymes. Zidovudine is an efficient substrate for the cellular thymidine kinase which converts it to AZT-MP in both infected and uninfected cells. AZT-MP accumulates in cells because of slow phosphorylation to AZT-DP by host-cell thymidylate kinase which is the rate-limiting step in AZT-TP formation. AZT-MP is a competitive inhibitor or thymidylate kinase and reduces the conversion of dTMP to dTDP which leads to decreased formation of dTTP. Other nucleoside analogs including ddI, ddC and ddA also have activity against HIV through a similar mechanism to that described for AZT.

However, the major toxicity of zidovudine is on the bone marrow, with macrocytic anemia and granulocytopenia common occurrences. The mechanisms of these toxic effects are uncertain. Rare instances of pancytopenia with hypocellular marrow have been described, and patients with poor bone marrow reserve, secondary to opportunistic infections or vitamin $B_{12}$ deficiency, have more toxicity than patients with sufficient marrow reserve. Nausea, myalgia, insomnia, fever, rash, nail pigmentation, and severe headaches may also be observed.

Reticulose[1] emerged as an antiviral product in the 1930's. While it was originally believed to be a product composed of peptone, peptides and nucleic acids, the precise composition remains unidentified. Nevertheless, Reticulose has demonstrated an ability to inhibit rapidly the course of several viral diseases. It is nontoxic, miscible with tissue fluids and blood sera and free from anaphylactogenic properties. Product R is a refinement of the original Reticulose prepared by an improved manufacturing process. It is a peptide nucleic acid preparation with a defined composition. Recent studies demonstrated that Product R can also stimulate the immune system and red blood cell production, suggesting that Product R is an immune system modulator.

1. Reticulose is a trademark of Advanced Viral Research Corp.

Insofar as the applicant knows, Product R has never been used, nor suggested for treating AIDS patients in combination with other anti-AIDS agents. It is now discovered that a combination of Product R and other antiviral agents useful for treating HIV infections or AIDS presents an advantageous treatment for AIDS patients.

Most infectious diseases caused by bacteria antimicrobialgents (antibiotics) are administered to attack a metabolic pathway in the invading bacteria so as to rapidly decrease the inoculum size of the infecting organism (the number of bacteria). The decrease in the inoculum size of the infecting bacterium allows the immune system to come in and mop up, that is, remove the last vestiges of the infecting organism. Therefore, a functioning immune system is vital for treatment of most infectious diseases.

One way of treating patients infected with HIV, as shown in the present application, is to quickly decrease the viral load by administering nucleoside analogues, for example, azidothymidine and lamivudine, together with a protease inhibitor to quickly decrease the viral load by attacking the replicative pathway of the virus directly, while administering Product R to stimulate both the bone marrow and cytocidal arm of the immune system. When the viral load has reached zero or reaches a low plateau the nucleoside analogues and the protease inhibitor are discontinued and the patient is continued on Product R therapy alone. This removes the potential side effects of the nucleoside analogues and protease inhibitor including the inhibiting immune function. On Product R therapy alone, now faced with a viral load of zero in the blood stream, the immune system has a much better chance for repair and to mop up the vestiges of viral infections.

SUMMARY OF THE INVENTION

Accordingly, an object of this invention is to provide a method for treating a patient having AIDS or HIV infections by administering an effective treatment amount of Product R in combination with one or more antiviral agents useful for treating AIDS or HIV infections, such as nucleoside analogs, to the patient.

Another object of the present invention is to provide a method for treating a patient having AIDS or HIV infections by a combination of an effective treatment amount of Product R and one or more nucleotide analogs and/or HIV protease inhibitors.

According to the present invention, the identified patient is treated by administering parenterally an effective treatment amount of Product R from about 5 microliters to about 40 microliters per kilogram of body weight per day in a sterile injectable formulation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE PRESENTLY PREFERRED EMBODIMENTS

As used herein, Product R is the product produced according to either of the following methods.

Method I For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II For Preparing Product R

Suspend about 35.0 g of casein, about 17.1 g of beef peptone, about 22.0 g of nucleic acid (RNA), about 3.25 g bovine serum albumin in about 2.5 liter of water for injection USP at about 3 to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCL (reagent grade ACS) or 35% (w/v) of NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

HIV protease inhibitors include oligopeptide analogs, such as saquinavir (Roche Laboratories), indinavir (Merck)

or ritonavir (Abbott Laboratories), which are fully described in detail in U.S. Pat. Nos. 5,413,999 and 5,476,874. The contents of which are hereby incorporated by reference in their entirety.

The antiviral agents useful for a combination therapy of AIDS or HIV infections other than HIV protease inhibitors is listed in Table I.

TABLE I

| Drug Name | Manufacturer | Indication |
|---|---|---|
| AL-721 | Ethigen (Los Angeles, CA) | ARC, PGL HIV positive, AIDS |
| Recombinant Human Interferon Beta | Triton Biosciences (Almeda, CA) | AIDS, Kapsi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxythymidine | Bristol-Myers (New York, NY) | AIDS, ARC |
| ddI Dideoxyinosine | Bristol-Myers (New York, NY) | AIDS, ARC |
| EL10 | Elan Corp. PLC Gainesville, GA) | HIV infection |
| Trisodium Phosphonoformate | Astra Pharm. Products, Inc. (Westborough, MA) | CMV retinitis, HIV infection, other CMV infections |
| Dideoxycytidine ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive, asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination with Retrovir |
| Acyclovir | Burroughs Wellcome | AIDS, ARC, asymptomatic HIV positive, in combination with AZT. |
| Antibody which neutralizes pH labile alpha aberrant Interferon in an inimuno-adsorption column | Advanced Biotherapy Concepts (Rockville, MD) | AIDS, ARC |
| L-697,661 | Merck (Rahway, NJ) | AIDS, ARC, asymptomatic HIV positive, also in combination with AZT. |

TABLE I-continued

| Drug Name | Manufacturer | Indication |
|---|---|---|
| L-696,229 | Merck (Rahway, NJ) | AIDS, ARC, asymptomatic HIV positive, also in combination with AZT. |
| Lamivudine | Glaxo (Research Triangle Park, NC) | HIV |
| Nevirapine | Roxane (Columbus, OH) | HIV |

It will be understood that the scope of combinations of Product R with antiviral agents is not limited to the list in the above Table I or described above, but includes in principle any combination with any pharmaceutical composition useful for treating patients having AIDS or HIV infections.

Preferred combinations are concurrent or alternating treatments of one or more HIV protease inhibitors or antiviral agents useful for treating AIDS or HIV in forms of nucleoside analogs, such as AZT, ddI or ddC, and Product R. Preferably, the HIV protease inhibitors or antiviral agents useful for treating AIDS or HIV infections are administered first, e.g. for one week, to quickly decrease the viral load; Product R then is administered to stimulate the immune system to eradicate the HIV infections. For patients who are very ill with opportunistic infections, Product R may be administered to stimulate the immune system first before and then after the indicated antiviral agents are applied.

Alternatively, two antiviral agents useful for treating AIDS or HIV such as lamivudine and AZT, together with one protease inhibitor such as ritonavir, may be administered concurrently first until the viral load is no longer measurable, then Product R is administered to eradicate the HIV infections.

Or, Product R may be administered concurrently with two antiviral agents such as lamivudine and nevirapone, one protease inhibitor such as indinavir.

For the patient having HIV infections, whether exhibiting AIDS symptoms or having antibodies against HIV or having asymptomatic infections, a suitable effective dose of Product R may be in the range of from about 5 microliters to about 40 microliters per kilogram of body weight per day, preferably in the range of about 10 microliters to about 25 microliters per kilogram of body weight per day. Most preferably Product R is administered in an amount of about 30 microliters per kilogram of body weight per day for about one week, followed by about 15 microliters per kilogram of body weight per day in a sterile injectable formulation. The desired dose may be administered as two, three or more sub-doses at appropriate intervals, generally equally spread in time throughout the day. Preferably, the full daily dose is administered in one administration.

The dose of the antiviral agents or HIV protease inhibitors to be co-administered with Product R can be readily determined by those skilled in the art, based on the usual patient symptoms, and severity of the diseases.

Product R may be administered by any suitable injection route including, but not limited to, intravenously, intraperitoneally, subcutaneously, intramuscularly, and intradermally, etc. The presently preferred route of administration is intramuscularly. It will be appreciated that the preferred route may vary with, for example, the condition and age of the recipient.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations may conveniently be presented in unit-dose or multi-dose containers, e.g. sealed ampules and vials.

Thus, while there have been shown and described and pointed out fundamental novel features of the invention as applied to preferred embodiments thereof, it will be understood that various omissions and substitutions and changes in the form and details of the method illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

The following example serves to illustrate the present invention and should not limit the scope of the invention.

EXAMPLE

The patient M. S. is a 38 year old Caucasian male who contracted AIDS through heterosexual contact some four years ago. The patient lives in Paris.

The Patient has been treated at a large AIDS clinic in Paris with three drug therapy consisting of azidothymidine, lamivudine and a protease inhibitor. He did not tolerate this therapy and was therefore noncompliant with the therapy. Moreover, when the three drugs were last administered, the viral load continued to rise despite the three-drug therapy. The patient had severe diarrhea, was cachectic, and was covered with an ulcerated dermatitis over his body (eczematoid—like dermatitis). The patient had suffered multiple opportunistic infections. His viral load was 500,000 per ml and the CD4 cell count was 10 per microliter.

The patient was then treated with a combination of azidothymidine (AZT), lamivudine (3-TC), and viracept (inhibitor of HIV protease) at commonly used dosages and administration route together with Product R at a dose of 1 ml subcutaneously per day for about one month, which reduced his viral load to 50,000 per ml.

Thereafter, the combination administration of AZT, 3-TC and viracept was discontinued and the patient was treated with Product R alone at a dose of 1 ml subcutaneously per day for more than four months. At the fourth month on Product R alone, the patient had no measurable viral load and the CD4 cell count was 49 cells per microliter.

No toxic side effects were observed during the period of Product R alone therapy.

I claim:

1. A method for reducing human immunodeficiency viral load while increasing CD4 cell count in a patient having acquired immunodeficiency syndrome (AIDS) resulting from human immunodeficiency virus (HIV) infection, comprising the steps of:
    (a) administering to said patient an effective HIV infection treatment mount of a Product R and an effective HIV infection treatment amount of at least one other antiviral agent useful for treating HIV infection comprising at least one nucleoside analog; and
    (b) discontinuing said administration of said one other antiviral agent and continuing to administer said effective HIV infection treatment amount of a Product R to said patient following step (a);
    wherein said Product R is produced according to Method I, and wherein the step of using about 16.5 g of sodium hydroxide for preparing said Product R is employed.

2. The method of claim 1, wherein said at least one other antiviral agent useful for treating HIV infection comprises at least one nucleoside analog and at least one inhibitor of HIV protease.

3. The method of claim 2, wherein said at least one nucleoside analog comprises azidothymidine and lamivudine, and said at least one inhibitor of HIV protease comprises viracept.

4. A method for reducing human immunodeficiency viral load while increasing CD4 cell count in a patient having acquired immunodeficiency syndrome (AIDS) resulting from human immunodeficiency virus (HIV) infection, comprising the steps of:
    (a) administering to said patient an effective HIV infection treatment amount of a Product R and an effective HIV infection treatment amount of at least one other antiviral agent useful for treating HIV infection comprising at least one nucleoside analog for about one month; and
    (b) discontinuing said administration of said one other antiviral agent and continuing to administer said effective HIV infection treatment amount of a Product R to said patient following step (a) for at least 4 months;
    wherein said Product R is produced according to Method I, and wherein the step of using about 16.5 g of sodium hydroxide for preparing said Product R is employed.

5. The method of claim 4, wherein said at least one other antiviral agent useful for treating HIV infection comprises at least one nucleoside analog and at least one inhibitor of HIV protease.

6. The method of claim 5, wherein said at least one nucleoside analog comprises azidothymidine and lamivudine, and said at least one inhibitor of HIV protease comprises viracept.

* * * * *